US00RE34189E

United States Patent [19]

Harandi

[11] E Patent Number: Re. 34,189

[45] Reissued Date of Patent: Mar. 2, 1993

[54] CONVERSION OF PARAFFINS TO GASOLINE

[75] Inventor: Mohsen N. Harandi, Lawrenceville, N.J.

[73] Assignee: Mobil Oil Corporation, Fairfax, Va.

[21] Appl. No.: 645,421

[22] Filed: Jan. 11, 1991

Related U.S. Patent Documents

Reissue of:

[64] Patent No.: 4,788,364
Issued: Nov. 29, 1988
Appl. No.: 137,112
Filed: Dec. 22, 1987

[51] Int. Cl.[5] ..... C07C 1/00; C07C 12/00; C07C 2/02

[52] U.S. Cl. ..... 585/312; 208/64; 208/65; 208/66; 422/190; 422/191; 585/322; 585/330; 585/412; 585/517

[58] Field of Search ..... 585/312, 322, 330, 412, 585/517; 208/64, 65, 66; 422/190, 191

[56] References Cited

U.S. PATENT DOCUMENTS 3,827,968 8/1974 Givens et al. ..... 208/49
4,542,247 9/1985 Chang et al. ..... 585/533

*Primary Examiner*—Anthony McFarlane
*Attorney, Agent, or Firm*—Alexander J. McKillop; Charles J. Speciale; Robert B. Furr, Jr.

[57] ABSTRACT

An improved two-step process for the conversion of lower molecular weight paraffins, the process comprising contacting in a first step a $C_2$–$C_{10}$ alkane-rich feedstock with a siliceous zeolite catalyst in a primary fluidized bed reaction zone under high temperature dehydrogenation conditions to obtain an intermediate product comprising oligomerizble olefinic hydrocarbons and aromatics; and then contacting in a second step the intermediate product with a siliceous zeolite catalyst in a secondary fluidized bed reaction zone under low temperature oligomerization conditions to obtain a final product comprising gasoline boiling range aliphatic and aromatic hydrocarbons.

39 Claims, 4 Drawing Sheets

CONVERSION OF PARAFFINS TO GASOLINE

Matter enclosed in heavy brackets [ ] appears in the original patent but forms no part of this reissue specification; matter printed in italics indicates the additions made by reissue.

BACKGROUND OF THE INVENTION

In a modern petroleum refinery several process units generate hydrocarbon byproducts of low commercial value. Side streams comprising lower molecular weight paraffins are generally low in value and often burned as a source of fuel.

Efforts to upgrade hydrocarbon streams containing $C_2$–$C_{10}$ paraffins have included contacting the paraffins under high severity dehydrocyclization conditions with a crystalline shape selective medium pore siliceous acid catalyst in a fluidized bed reaction zone to obtain aromatic hydrocarbons such as benzene, toluene and isomeric xylenes (BTX). Such an operation provides a convenient one-step route for producing an aromatics-rich gasoline with a relatively high octane number.

U.S. Pat. No. 3,827,968 (Givens et al) discloses a two-stage operation wherein a mixed feed containing paraffins and olefins is upgraded in the absence of added hydrogen to a highly aromatic gasoline product. In a first stage oligomerization reaction, olefins are upgraded to higher molecular weight liquid hydrocarbons under relatively mild conditions with a catalyst having the structure of ZSM-5. In a second stage, said liquid hydrocarbons are converted to an aromatic product. A gas phase highly paraffinic stream is withdrawn as byproduct from the first stage.

SUMMARY OF THE INVENTION

The invention integrates a dehydrocyclization process operated at mild conditions with an oligomerization-aromatization process to efficiently convert $C_2$–$C_{10}$ paraffins to highly aromatic and olefinic gasoline having a high octane rating. In a preferred process of the invention, a dual fluidized bed vertical column reactor comprising a lower transport riser reaction zone and an upper turbulent flow reaction zone, both zones containing fluidized catalyst comprising acid medium pore metallosilicate zeolite, is maintained for contacting the paraffinic feed with catalyst. The feed enters the dual column reactor at the lower transport riser reaction zone under high temperature dehydrogenation conditions to substantially prevent cracking reactions. An intermediate product comprising dehydrogentated hydrocarbons and aromatics leaves the lower zone and enters the upper turbulent zone operated at conditions to enhance oligomerization. A final product comprising gasoline boiling range hydrocarbons is obtained.

Accordingly, it is a primary object of this invention to provide a process for converting lower molecular weight alkanes to gasoline by dehydrogentaion of $C_2$–$C_{10}$ paraffins to form olefins, feeding the olefins to an oligomerization zone, and converting the olefins to a valuable gasoline product in the oligomerization zone.

DETAILED DESCRIPTION OF THE INVENTION

It is known in the art that lower molecular weight alkanes can be efficiently upgraded to valuable hydrocarbon products by contacting the alkanes under high severity dehydrocyclization conditions with an acid catalyst having the structure of ZSM-5. A number of chemical reactions, such as dehydrogenation, oligomerization, alkylation, and aromatization, are occurring at such operating conditions. In this one-step process, paraffinic feedstock is converted to aromatic hydrocarbons comprising BTX.

An improved process has been discovered for converting $C_2$–$C_{10}$ paraffins to gasoline boiling range hydrocarbon product without the use of high severity dehydrocyclization conditions and with the concomitant increase in volumetric yield and octane-BBL rating of the product.

Figure 1:
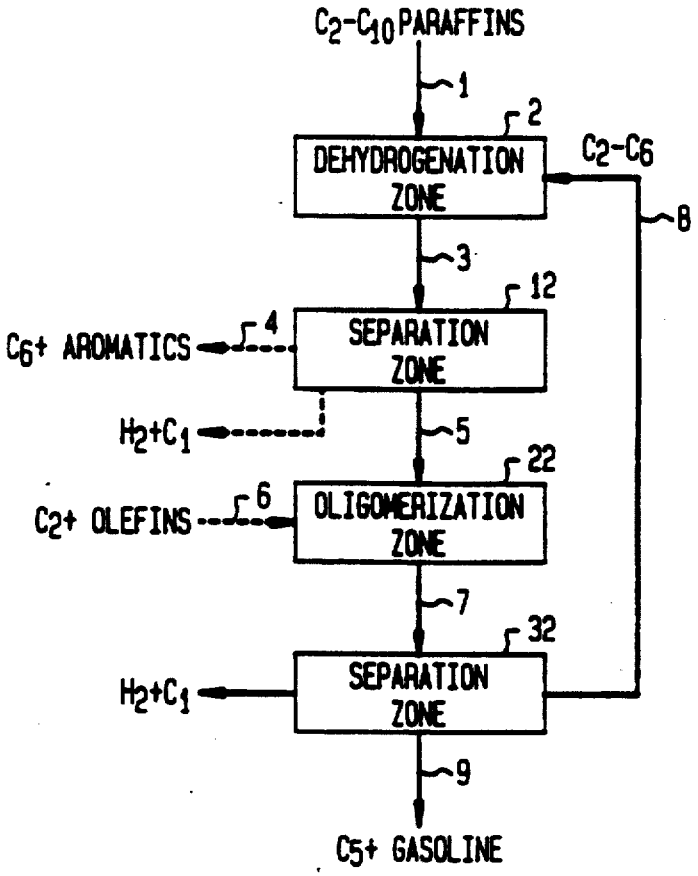
FIG. 1 is a process flow sheet showing the overall operation of the invention.

In FIG. 1, the overall process of the invention is shown in flow diagram form. A $C_2$–$C_{10}$ paraffinic stream is fed via line 1 to a dehydrogenation zone 2 to obtain an effluent rich in a oligomerizable hydrocarbons. The effluent is withdrawn via passage 3 and enters separation zone 12 where an aromatics-rich stream is optionally withdrawn by means 4. The stream rich in aromatics can be added to the final gasoline product obtained via line 9.

An intermediate product comprising olefinic hydrocarbons either with or without aromatics made in the first stage 2 enters oligomerization zone 22 by means of line 5. Optionally, a co-feed comprising $C_2$+ olefin-rich stream can be added as by means 6 to oligomerization zone 22 to convert olefins to gasoline.

A final product comprising gasoline boiling range hydrocarbons and unreacted paraffins enters separation zone 32 by means of inlet 7. A $C_5$+ gasoline product is withdrawn by means of outlet 9. Unreacted $C_2$–$C_6$ component such as paraffins and olefins are collected and recycled via line 8 to the dehydrogenation zone 2.

Figure 2:
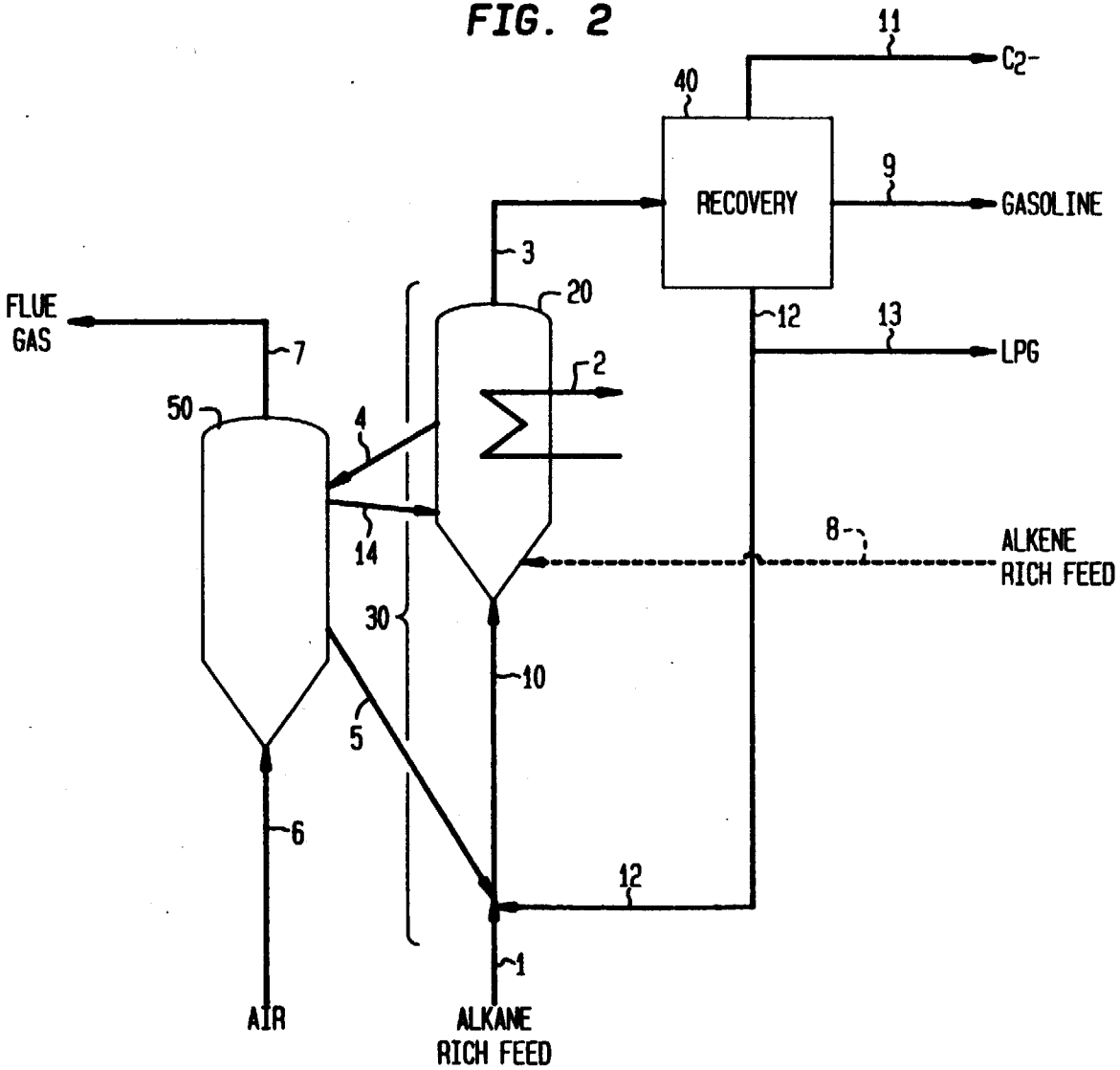
FIG. 2 is a diagram of a preferred process of the invention with dual reaction zones enclosed in a single reactor tower.

Referring to FIG. 2, a feedstream rich in $C_2$–$C_4$ alkanes is injected via passage 1 into a dual reactor vertical column 30. In a preferred example, $C_2$–$C_4$ alkanes are contacted with a ZSM-5 catalyst in a transport riser reaction zone 10 which comprises the lower portion of vertical reactor 30 under dehydrogenation conditions comprising a temperature of about 537° C. to 895° C. and a pressure of about 50 to 2000 kPa and a WHSV of 1 to 1000 to covert less than about 80 wt. % of $C_2$–$C_4$ alkanes to intermediate olefinic product.

The intermediate product comprising oligomerizable olefins, aromatics, and unreacted paraffins can be contacted directly with a catalyst having the structure of ZSM-5 in a turbulent flow fluidized bed reaction zone 20 which comprises the upper portion of vertical reactor 30 to convert greater than about 80 wt % intermediate olefins. Operating conditions for the turbulent flow reaction zone are based on typical MOG (Mobil Olefins to Gasoline) technology and comprise temperatures of about 215° C. to 535° C. and pressures of about 50 to 2000 kPa and a WHSV of about 0.1–10. The catalyst, which preferably comprises ZSM-5, may have an acid cracking value of about 2 to 35, preferably about 5-10. Thermal balance can be maintained by employing a heat exchange line 2 containing steam or preheated feedstock. Optionally, a co-feed comprising $C_2+$ alkenes can be introduced by means of line 8 to the upper turbulent oligomerization zone. This stream may also be used as a quench to maintain thermal balance in the fluid bed without using exchange line 2.

A product comprising $C_5+$ gasoline range hydrocarbons and unreacted alkanes is withdrawn via line 3 and enters recovery zone 40 where a gasoline stream is recovered as by line 9 and an overhead hydrogen rich $C_2-$ stream is withdrawn as by line 11.

Catalyst is withdrawn via line 4 and enters regeneration zone 50 for oxidative rejuvenation with an oxygen-containing gas such as air entering as by means 6. Freshly regenerated catalyst is combined with paraffinic feed via line 5 for contacting in the dehydrogenation zone 10. A portion of the regenerated catalyst can be sent directly to reaction zone 20 via line 14. Flue gas is withdrawn from catalyst regeneration zone via means 7.

Enhancement of overall process economy can be achieved by employing the same catalyst in both the lower transport zone 10 and the upper turbulent zone 20. As catalyst is partially deactivated it is transported from the lower zone to the upper zone where it functions as an olefins oligomerization and aromatization catalyst.

The catalysts preferred for use herein include crystalline aluminosilicate zeolites having a silica-to-alumina ration of at least 12, a Constraint Index of about 1 to 12 and acid cracking activity of about 16-200. Representative of suitable zeolites are ZSM-5, ZSM-11, ZSM-12, ZSM-23, and ZSM-35. ZSM-5 is disclosed and claimed in U.S. Pat. No. 3,702,886 and U.S. Pat. No. Re. 29,948; ZSM-11 is disclosed and claimed in U.S. Pat. No. 3,709,979. Also see U.S. Pat. Nos. 3,832,449 for ZSM-12; 4,076,842 for ZSM-23; 4,016,245 for ZSM-35. The disclosures of the above patents are incorporated herein by reference. A suitable shape selective catalyst is a HZSM-5 zeolite with alumina binder in the form of cylindrical extrudates. Other catalysts which may be used include a variety of medium pore (~5 to 8 Angstroms) siliceous materials, such as borosilicates, ferrosilicates and/or aluminosilicates, disclosed in U.S. Pat. Nos. 4,414,143 and 4,417,088, incorporated herein by reference.

It is not necessary to employ only medium pore metallosilicate zeolite catalysts in the reaction zones. A large pore zeolite material can be used.

The medium pore shape selective aluminosilicate catalyst can contain other materials, such as P, Ga, Sn, Re, Zn, Pt, and Cu, which are incorporated in the catalyst by known procedures such as ion exchange, etc.

Figure 3:
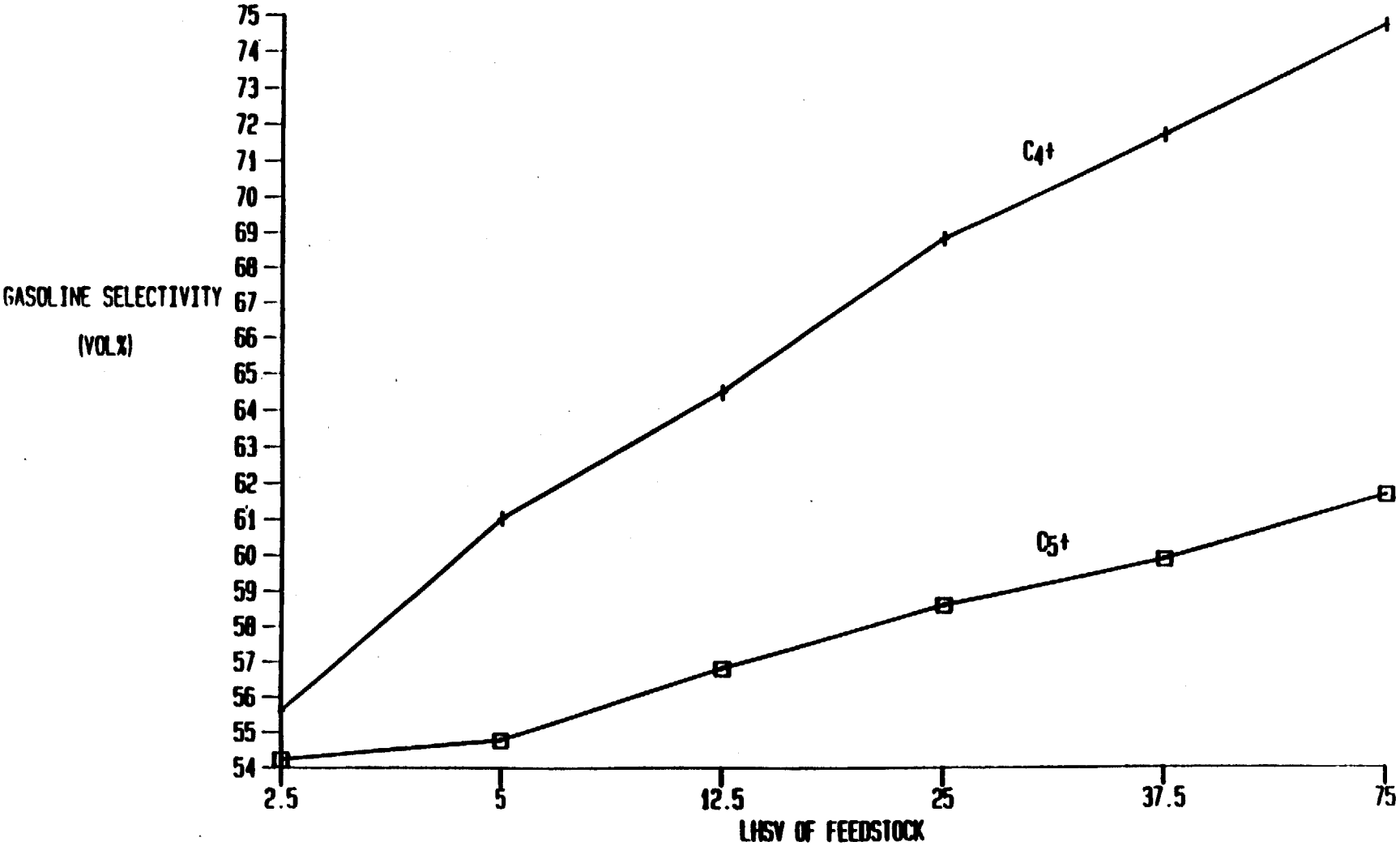
FIG. 3 is a graph of gasoline selectivities versus operational space velocity.

Referring to FIG. 3, selectively for both $C_4+$ gasoline and $C_5+$ gasoline is plotted against the operational space velocity in a dehydrocyclization reaction employing a saturated lower aliphatic feedstock. Conditions of temperature and pressure are maintained as constants. Conventional gasoline-from-paraffins operations employ preferably a maximum LHSV of about 2.5, while the process of the present invention preferably employs a LHSV of about 25. The present process increases $C_5+$ gasoline selectively about 10% by volume based on feedstock; and the $C_4+$ gasoline selectively is increased about 20% by volume based on feedstock.

Figure 4:
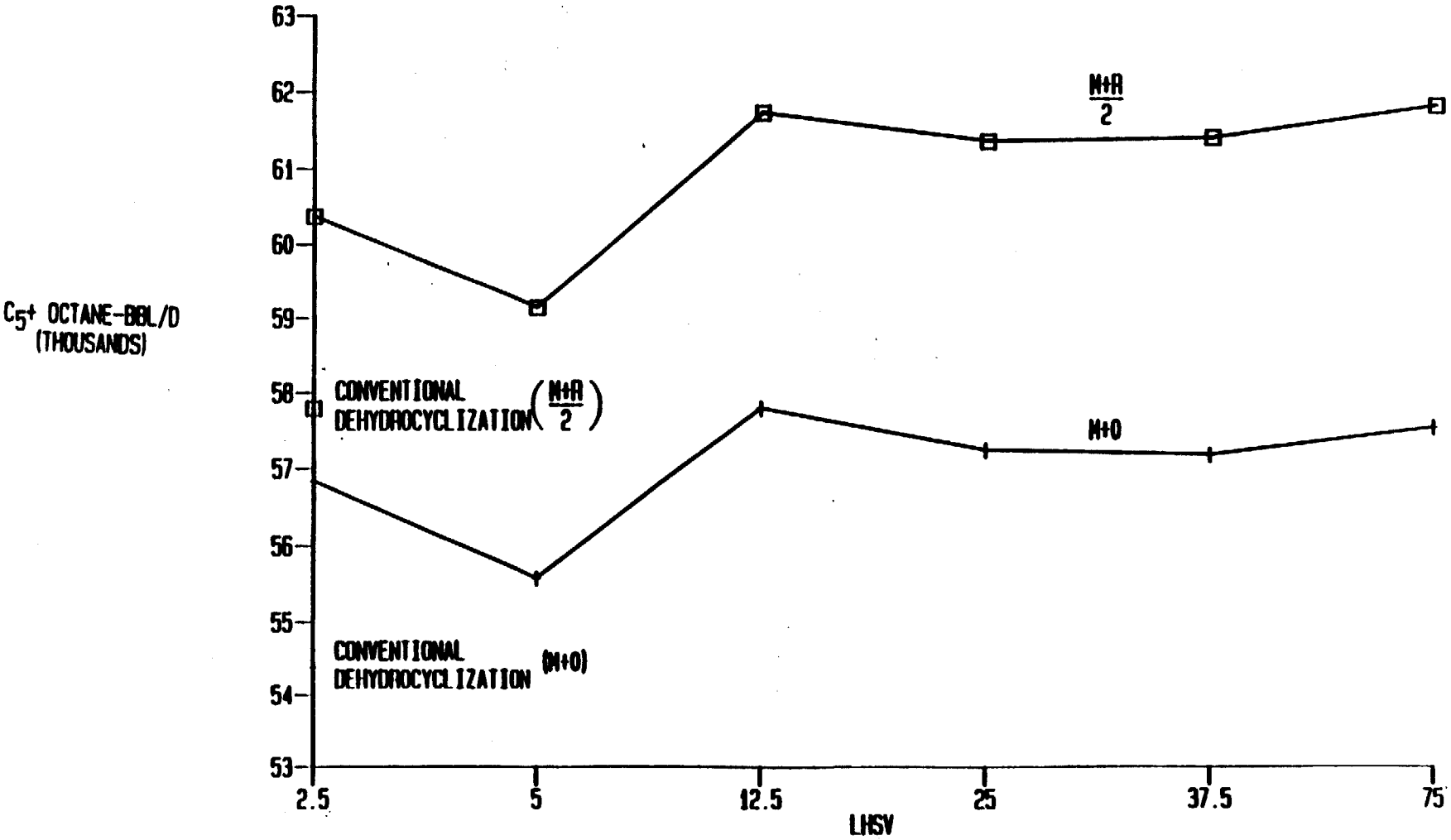
FIG. 4 is a graph of $C_5$+ gasoline octane-BBL versus operational space velocity.

In FIG. 4 $C_5+$ gasoline octane-BBL is plotted against the liquid hourly spaced velocity of a feedstock comprising saturated lower molecular weight hydrocarbons. In standard dehydrocyclization reactions, the preferred maximum LHSV of paraffinic feedstock is about 2.5 $hr.^{-1}$ which gives a product with $C_5+$ gasoline octane-BBL ratings of about 54.5 (M+0) and about 60.5 (M+R/2). When the LHSV of the feedstock is increased in accordance with the present process, $C_5+$ gasoline-BBL ratings are increased significantly.

In the process for dehydrocyclization of a parafinic feedstock comprising $C_2$–$C_{10}$ alkanes in a primary fluidized bed reaction zone over a catalyst comprising crystalline medium pore acid siliceous zeolite under high severity conversion conditions of WHSV, temperature, and pressure to obtain an aromatic product comprising benzene, toluene and/or xylenes, the improvement of the present invention comprises optimizing the operating severity by adjusting the space velocity and temperature in the primary reaction zone to effect partial conversion of the paraffinic feedstock, thereby effectively dehydrogenating the $C_2$–$C_{10}$ alkanes to obtain an intermediate product comprising maximum lower olefins plus aromatics, adding a secondary fluidized bed reaction zone in series with the primary reaction zone, the secondary reaction zone containing a catalyst comprising crystalline medium pore acid siliceous zeolite; and contacting the intermediate product in the secondary fluidized bed reaction zone over the siliceous catalyst under oligomerization conditions to obtain a final product comprising $C_5+$ gasoline boiling range aliphatic and aromatic hydrocarbons and unconverted alkanes.

In the primary reaction zone less than about 75 wt. % of $C_2$–$C_{10}$ alkane is converted to intermediate product; and in the secondary reaction zone greater than about 90 wt. % of intermediate lower olefinic product is converted to $C_5+$ gasoline boiling range aliphatic and aromatic hydrocarbons.

To increase output of gasoline product, it is desirable to introduce an auxiliary feedstock comprising oligomerizable lower olefins to the secondary reaction zone, withdrawing final product from the secondary fluidized bed reaction zone and separating the product to obtain a high octane gasoline. The unconverted alkanes separated from final product are recycled to the primary fluidized bed reaction zone for further conversion.

The $C_2$–$C_{10}$ alkane feedstock preferably comprises propane. Other suitable feedstocks are ethane, butane, pentane, and hexane in any of their isomeric forms, either alone or in admixture with one another. Another useful feed is the reformer paraffins separated in an extraction unit such as Udex. Other preferred feeds include the saturated gas plant LPG as the paraffinic feedstock and the USGP LPG with or without the ethene fraction as the olefinic feedstock.

In the alternative, the lower molecular weight oligomerizable olefins can be added to the intermediate product prior to contact in the secondary fluidized bed reaction zone. Examples of lower molecular weight oligomerizable olefins are ethene, propene, the isomeric butenes, pentenes, and hexenes. The olefin can be added individually or in mixtures.

The crystalline medium pore siliceous catalyst in the primary reaction zone preferably comprises a zeolite having the structure of ZSM-5. Most preferably, the catalyst comprises HZSM-5.

In the secondary reaction zone, the crystalline medium pore siliceous catalyst preferably comprises a zeolite having the structure of ZSM-5. Most preferably, the catalyst comprises HZSM-5.

The high severity reaction conditions in the primary fluidized bed reaction zone comprise a temperature of about 537° C., a pressure of about 50 to 2000 kPa, and a catalyst acid cracking value of about 5 to 50. The oligomerization conditions in the secondary fluidized bed reaction zone comprise a temperature of about 215° C. to 535° C., a pressure of about 50 to 2000 kPa, and a catalyst acid cracking value of about 2 to 10.

In a preferred embodiment, the present invention relates to a process for the conversion of $C_2$–$C_{10}$ alkanes to olefinic and aromatic hydrocarbons boiling in the gasoline range comprising: contacting a feedstock comprising at least one $C_2$–$C_{10}$ alkane with a catalyst comprising crystalline medium pore acid siliceous zeolite in a primary fluidized bed reaction zone under high temperature dehydrogenation conditions to substantially prevent cracking reactions to obtain an intermediate product comprising dehydrogenated hydrocarbons and aromatics; and contacting the intermediate product with a catalyst comprising crystalline medium pore acid siliceous zeolite in a secondary fluidized bed reaction zone under lower temperature oligomerization conditions to obtain a final product comprising gasoline boiling range hydrocarbons and unreacted $C_2$–$C_{10}$ alkane.

The following example is intended to illustrate the benefits of the present two-stage process.

EXAMPLE

A paraffinic hydrocarbon feedstock comprising FCC light gasoline is contacted under dehydrocyclization conditions with a shape selective acidic metallosilicate zeolite catalyst. The liquid hourly space velocity of the feedstock is increased in stage from 2.5 hr.$^{-1}$ to 75 hr.$^{-1}$. At increasing LHSV, total aromatics production decreases and production of reactive olefins is increased as represented in Table 1 below. Operation of a dehydrocyclization reaction at relatively high LHSV produces an olefinic hydrocarbon product which is then oligomerized in a second stage to obtain high quality gasoline. In addition, gas make is significantly reduced reaction heat input requirements are reduced, catalyst make-up rate is reduced, benzene concentration in the final gasoline product is reduced, hydrogen purity is increased, and product recovery is less expensive.

TABLE 1

| LHSV | 2.5 | 5.0 | 12.5 | 25.0 | 37.5 | 75.0 |
|---|---|---|---|---|---|---|
| (Wt. %) | | | | | | |
| $H_2$ | 1.9 | 1.9 | 1.9 | 1.3 | 1.0 | 0.5 |
| methane | 10.8 | 4.3 | 3.0 | 1.7 | 1.4 | 0.8 |
| ethene | 2.0 | 6.5 | 8.1 | 8.6 | 10.0 | 9.5 |
| ethane | 8.2 | 7.2 | 4.9 | 3.5 | 2.3 | 1.7 |
| propene | 1.5 | 7.6 | 10.2 | 13.5 | 15.7 | 19.2 |
| propane | 9.5 | 11.7 | 11.6 | 11.3 | 10.4 | 8.8 |
| butanes | 1.5 | 6.9 | 7.7 | 13.3 | 14.8 | 14.4 |
| pentanes | 4.3 | 3.2 | 3.8 | 7.8 | 10.4 | 13.5 |
| total aromatics | 60.7 | 51.1 | 48.7 | 39.4 | 34.3 | 26.9 |
| benzene | 14.5 | 12.5 | 8.4 | 5.9 | 5.5 | 3.1 |
| toluene | 30.5 | 25.1 | 22.3 | 17.9 | 15.3 | 14.2 |
| xylenes | 12.1 | 10.8 | 13.2 | 11.8 | 10.3 | 6.5 |
| $C_{9+}$ aromatics | 3.6 | 2.7 | 4.8 | 3.8 | 3.2 | 3.1 |

Table 2 shows the product selectively when the two-stage alkane conversion reaction is compared with the conventional one-stage dehydrocyclization reaction. The product selectivity is shown in pounds per hour (Lbs/hr) and barrels per day (BPD).

TABLE 2

| | One-Stage Reaction | Two-Stage Reaction | | | | | |
|---|---|---|---|---|---|---|---|
| LHSV | 2.5 | 2.5 | 5 | 12.5 | 25 | 37.5 | 75 |
| Lbs/hr | | | | | | | |
| $C_4$ | 150 | 120 | 520 | 640 | 880 | 1010 | 1120 |
| disomerized $C_{5+}$* | 430 | 740 | 1630 | 2000 | 2990 | 3560 | 4240 |
| Benzene | 1440 | 1440 | 1240 | 840 | 590 | 550 | 330 |
| Toluene | 3030 | 3030 | 2490 | 2240 | 1780 | 1520 | 1490 |
| Xylene | 1200 | 1200 | 1070 | 1320 | 1170 | 1030 | 680 |
| $C_{9+}$ | 360 | 360 | 270 | 480 | 380 | 320 | 330 |
| Total $C_{5+}$ | 6460 | 6770 | 6700 | 6880 | 6910 | 6980 | 7070 |
| Total $C_{4+}$ | 6610 | 6890 | 7220 | 7520 | 7790 | 7990 | 8190 |
| BPD | | | | | | | |
| $C_4$ | 17.08 | 14.63 | 61.63 | 75.83 | 104.04 | 118.89 | 132.45 |
| disomerized $C_{5+}$* | 39.91 | 68.68 | 151.29 | 185.63 | 277.52 | 330.42 | 393.54 |
| Benzene | 111.51 | 111.51 | 96.02 | 65.05 | 45.69 | 42.59 | 25.55 |
| Toluene | 238.04 | 238.04 | 195.62 | 175.98 | 139.84 | 119.41 | 117.06 |
| Xylene | 94.48 | 94.48 | 84.24 | 103.93 | 92.12 | 81.10 | 53.54 |
| $C_{9+}$ | 28.67 | 28.67 | 21.51 | 38.23 | 30.27 | 25.49 | 26.28 |
| Total $C_{5+}$ | 512.62 | 541.39 | 548.68 | 568.82 | 585.43 | 599.01 | 615.97 |
| Total $C_{4+}$ | 529.70 | 556.02 | 610.31 | 644.65 | 689.47 | 717.90 | 748.42 |
| $C_{5+}$ (R + O) | 119.2 | 118.0 | 114.2 | 115.2 | 111.5 | 109.1 | 107.0 |
| $C_{5+}$ (M + O) | 106.4 | 105.1 | 101.2 | 101.5 | 97.7 | 95.4 | 93.4 |
| $C_{5+}$ (ROAD) | 112.8 | 111.6 | 107.7 | 108.3 | 104.6 | 102.3 | 100.2 |
| R + O (BBLS/D) | 61103 | 63879 | 62664 | 65502 | 65254 | 65366 | 65927 |
| M + O (BBLS/D) | 54517 | 56908 | 55553 | 57709 | 57198 | 57169 | 57529 |
| ROAD (BBLS/D) | 57810 | 60394 | 59108 | 61606 | 61226 | 61267 | 61728 |

*Includes non aromatic $C_{5+}$ made in the first stage reaction plus total $C_{5+}$ made in the second stage reaction.

Composition of $C_5$+ gasoline product is shown in a comparative fashion in Table 3 for both the conventional one-stage dehydrocyclization reaction and the two-stage alkane conversion reaction of the present invention.

TABLE 3

| | One-Stage Reaction | Two-Stage Reaction | | | | | |
|---|---|---|---|---|---|---|---|
| LHSV | 2.5 | 2.5 | 5 | 12.5 | 25 | 37.5 | 75 |
| disomerized $C_{5+}$, Vol % | 7.79 | 12.69 | 27.57 | 32.63 | 47.40 | 55.16 | 63.89 |
| Benzene, Vol % | 21.75 | 20.60 | 17.50 | 11.44 | 7.80 | 7.11 | 4.15 |
| Toluene, Vol % | 46.44 | 43.97 | 35.65 | 30.94 | 23.89 | 19.94 | 19.00 |

TABLE 3-continued

| | One-Stage Reaction | Two-Stage Reaction | | | | | |
|---|---|---|---|---|---|---|---|
| LHSV | 2.5 | 2.5 | 5 | 12.5 | 25 | 37.5 | 75 |
| Xylene, Vol % | 18.43 | 17.45 | 15.35 | 18.27 | 15.74 | 13.54 | 8.69 |
| $C_{9+}$, Vol % | 5.59 | 5.30 | 3.92 | 6.72 | 5.17 | 4.25 | 4.27 |
| Total | 100.00 | 100.00 | 100.00 | 100.00 | 100.00 | 100.00 | 100.00 |

While the invention has been described by specific examples and embodiments, there is no intent to limit the inventive concept except as set forth in the following claims.

What we claim is:

1. A continuous process for conversion of $C_2$–$C_4$ alkanes to aromatic rich hydrocarbons boiling in the gasoline range comprising:

maintaining a dual vertical column reactor comprising a lower transport riser reaction zone and an upper turbulent fluidized bed reaction zone, both zones containing fluidized catalyst comprising acid medium pore metallosilicate zeolite;

contacting a feedstock comprising at least one $C_2$–$C_4$ alkane with fluidized catalyst in the lower transport zone under high temperature dehydrogenation conditions to dehydrogenate the feedstock and substantially prevent cracking reactions to obtain an intermediate product comprising dehydrogenated hydrocarbons and aromatics; and contacting the intermediate hydrocarbon product with fluidized catalyst in the upper turbulent zone under lower temperature oligomerization conditions to obtain a final product comprising $C_5$+ gasoline boiling range hydrocarbons.

2. A process according to claim 1 wherein the $C_2$–$C_4$ alkane feedstock comprises propane, and the zeolite has the structure of ZSM-5 zeolite.

3. A process according to claim 1 wherein an auxiliary feedstock comprising oligomerizable olefins is added to the intermediate product for contact in the upper zone.

4. A process according to claim 1 wherein less than about 80 wt. % of $C_2$–$C_4$ alkane is converted to intermediate product in the lower transport zone.

5. A process according to claim 1 wherein greater than about 80 wt. % of dehydrogenated hydrocarbons converted to final product in the upper zone.

6. A process according to claim 1 wherein unreacted $C_2$–$C_4$ components are separated from final product and recycled to the lower transport zone for conversion.

7. A process according to claim 1 wherein the siliceous zeolite in both zones comprises HZSM-5.

8. A process according to claim 1 wherein deactivated catalyst is withdrawn from the upper turbulent flow reaction zone and contacted with an oxygen-containing gas for regeneration.

9. A process according to claim 8 wherein regenerated catalyst is added to the lower transport riser reaction zone.

10. A process according to claim 1 wherein reaction conditions in the lower transport zone comprise a temperature of about 537° C. to 895° C, a WHSV of 1–1000, and a pressure of about 50 to 2000 kPa.

11. A process according to claim 1 wherein reaction conditions in the upper turbulent zone comprise a WHSV of 0.1 to 10, temperature of about 215° C. to 535° C., and a pressure of about 50 to 2000 kPa.

12. A process according to claim 1 wherein the siliceous metallosilicate acid zeolite catalyst contained in the lower transport zone has an acid cracking value of about 5 to 50.

13. A process according to claim 1 wherein the siliceous metallosilicate acid zeolite catalyst contained in the upper turbulent zone has an acid cracking value of about 2 to 10.

14. A process according to claim 1 further comprising withdrawing the final product from the upper turbulent zone and separating the product to obtain a high octane gasoline.

15. In a process for dehydrocyclization of a paraffinic feedstock comprising $C_2$–$C_{10}$ alkanes in a primary fluidized bed reaction zone over a catalyst comprising crystalline medium pore acid siliceous zeolite under high severity conversion conditions of temperature and pressure to obtain an aromatic product comprising benzene, toluene and/or xylenes, the improvement comprising:

(a) optimizing the operating severity by adjusting the space velocity and temperature in the primary reaction zone to effect partial conversion of the paraffinic feedstock, thereby effectively dehydrogenating the $C_2$–$C_{10}$ alkanes to obtain an intermediate product containing maximum lower olefins and aromatics.

(b) adding a secondary fluidized bed reaction zone in series with the primary reaction zone, the secondary reaction zone containing a catalyst comprising crystalline medium pore acid siliceous zeolite; and (c) contacting the intermediate product in the secondary fluidized bed reaction zone over the siliceous catalyst under oligomerization conditions to obtain a final product comprising $C_5$+ gasoline boiling range aliphatic and aromatic hydrocarbons and unconverted alkanes.

16. A process according to claim 15 wherein the $C_2$–$C_{10}$ alkane comprises propane, and the zeolite catalyst in the primary and/or secondary reaction zone comprises a zeolite having the structure of ZSM-5.

17. A process according to claim 15 wherein an auxiliary feedstock comprising oligomerizable lower olefins is added to the secondary reaction zone.

18. A process according to claim 15 wherein less than about 80 wt. % of $C_2$–$C_{10}$ alkane is converted to intermediate product.

19. A process according to claim 15 wherein greater than about 80 wt. % of intermediate lower olefinic product is converted to $C_5$+ gasoline boiling range aliphatic and aromatic hydrocarbons.

20. A process according to claim 15 wherein unconverted alkanes are separated from final product and recycled to the primary fluidized bed reaction zone.

21. A process according to claim 15 wherein the high severity reaction conditions in the primary fluidized bed reaction zone comprise a WHSV of about 1–1000, a temperature of about 537° C. to 895° C., a pressure of about 50 to 2000 kPa, and a catalyst acid cracking value of about 5 to 50.

22. A process according to claim 15 wherein the oligomerization conditions in the secondary fluidized bed reaction zone comprise a WHSV of about 0.1–10, a temperature of about 215° C. to 535° C., a pressure of about 50 to 2000 kPa, and a catalyst acid cracking value of about 2 to 10.

23. A process according to claim 15 further comprising withdrawing final product from the secondary fluidized bed reaction zone and separating the product to obtain a high octane gasoline.

24. A process for the conversion of $C_2$–$C_{10}$ alkanes to aromatic rich hydrocarbons boiling in the gasoline range comprising:

contacting a feedstock comprising at least one $C_2$–$C_{10}$ alkane with a catalyst comprising crystalline medium pore acid siliceous zeolite in a primary fluidized bed reaction zone under high temperature dehydrogenation conditions to substantially prevent cracking reactions to obtain an intermediate product comprising aromatic and olefinic hydrocarbons; and contacting the intermediate product with a catalyst comprising crystalline medium pore acid siliceous zeolite in a secondary fluidized bed reaction zone under lower temperature oligomerization conditions to obtain a final product comprising gasoline boiling range hydrocarbons and unreacted $C_2$–$C_{10}$ alkane.

25. A process according to claim 24 wherein the $C_2$–$C_{10}$ alkane comprises propane.

26. A process according to claim 24 wherein the crystalline medium pore acid siliceous zeolite in the primary and/or secondary reaction zones comprises a zeolite having the structure of ZSM-5.

27. A process according to claim 24 wherein an auxiliary feedstock comprising lower molecular weight oligomerizable olefins is added to the intermediate product prior to contact in the secondary fluidized bed reaction zone.

28. A process according to claim 24 wherein less than about 80 wt. % of $C_2$–$C_{10}$ alkane is converted to intermediate product.

29. A process according to claim 24 wherein greater than about 80 wt. % of intermediate olefinic hydrocarbons are converted to final product.

30. A process according to claim 24 wherein unreacted $C_2$–$C_{10}$ alkane is separated from final product and recycled to the primary fluidized bed reaction zone.

31. A process according to claim 24 wherein the high temperature bed reaction zone comprise a WHSV of about 1–1000, a temperature of about 537° C. to 895° C., a pressure of about 50 to 2000 kPa, and a catalyst acid cracking value of about 5 to 50.

32. A process according to claim 24 wherein the lower temperature oligomerization conditions in the secondary fluidized bed reaction zone comprise a WHSV of about 0.1–10, a temperature of about 215° C. to 535° C., a pressure of about 50 to 2000 kPa, and a catalyst acid racking value of about 2 to 10.

33. A process according to claim 26 wherein the catalyst comprises HZSM-5.

34. A process according to claim 26 wherein the zeolite having the structure of ZSM-5 contains a metal cation selected from the group consisting of P, Ga, Sn, Re, Zn, Pt, and Cu.

35. A process according to claim 24 wherein an auxiliary feedstock comprising lower molecular weight oligomerizable olefins is added to the secondary fluidized bed reaction zone as a fluidized bed distributor while the intermediate product from the primary reaction zone is added to the secondary reaction zone at a point above the auxiliary feedstock.

36. A process according to claim 35 wherein the intermediate product added to the secondary reaction zone contains an amount of entrained catalyst particles from the primary reaction zone.

37. A process according to claim 35 wherein the intermediate product is separated from entrained catalyst particles prior to addition to the secondary reaction zone.

38. An apparatus for the continuous conversion of $C_2$–$C_4$alkanes to aromatic rich hydrocarbons boiling in the gasoline range comprising:

a dual vertical column reactor comprising a lower transport riser reaction zone and an upper turbulent fluidized bed reaction zone, both zone containing fluidized catalyst comprising acid medium pore metallosilicate zeolite;

means for contacting a feedstock comprising at least one $C_2$–$C_4$ alkane with fluidized catalyst in the lower transport zone under high temperature dehydrogenation conditions to dehydrogenate the feedstock and substantially prevent cracking reactions to obtain an intermediate product comprising dehydrogenated hydrocarbons and aromatics; and means for contacting the intermediate hydrocarbon product with fluidized catalyst in the upper turbulent zone under lower temperature oligomerization conditions to obtain a final product comprising $C_5$+ gasoline boiling range hydrocarbons.

39. An apparatus for the conversion of $C_2$–$C_{10}$ alkanes to aromatic rich hydrocarbons boiling in the gasoline range comprising:

means for contacting a feedstock comprising at least one $C_2$–$C_{10}$ alkane with a catalyst comprising crystalline medium pore acid siliceous zeolite in a primary fluidized bed reaction zone under high temperature dehydrogenation conditions to substantially prevent cracking reactions to obtain an intermediate product comprising aromatic and olefinic hydrocarbons; and means for contacting the intermediate product with a catalyst comprising crystalline medium pore acid siliceous zeolite in a secondary fluidized bed reaction zone under lower temperature oligomerization conditions to obtain a final product comprising gasoline boiling range hydrocarbons and unreacted $C_2$–$C_{10}$ alkane.

* * * * *

UNITED STATES PATENT AND TRADEMARK OFFICE

CERTIFICATE OF CORRECTION

PATENT NO. : Re. 34,189

DATED : March 2, 1993

INVENTOR(S) : Mohsen N. Harandi

It is certified that error appears in the above-identified patent and that said Letters Patent is hereby corrected as shown below:

Col. 9, line 47, claim 31: After "temperature" and before "bed" insert -- dehydrogenation conditions in the primary fluidized --

Signed and Sealed this

Twenty-third Day of November, 1993

Bruce Lehman

*Attest:*

BRUCE LEHMAN

*Attesting Officer*

*Commissioner of Patents and Trademarks*